United States Patent [19]

Saggiomo et al.

[11] Patent Number: 4,554,279
[45] Date of Patent: Nov. 19, 1985

[54] 5-(STRAIGHT CHAIN 3–12 CARBON ALKOXY)-8-QUINOLINAMINES AND THEIR USE FOR TREATMENT OF MALARIA

[75] Inventors: Andrew J. Saggiomo; Edward A. Nodiff, both of Philadelphia, Pa.

[73] Assignee: The United States of America as represented by the Secretary of the Army, Washington, D.C.

[21] Appl. No.: 478,816

[22] Filed: Mar. 31, 1983

Related U.S. Application Data

[63] Continuation of Ser. No. 229,487, Jan. 29, 1981, abandoned.

[51] Int. Cl.[4] .................... A61K 31/47; C07D 215/20
[52] U.S. Cl. .................................................. 514/311
[58] Field of Search ...................... 546/171; 424/258; 514/311

[56] References Cited

U.S. PATENT DOCUMENTS

| | | | |
|---|---|---|---|
| 1,879,538 | 9/1932 | Schonhofer et al. | 546/171 |
| 1,938,047 | 12/1933 | Schonhofer et al. | 546/171 |
| 2,477,479 | 7/1949 | Elderfield | 546/171 |
| 4,167,638 | 9/1979 | Chen et al. | 546/157 |

OTHER PUBLICATIONS

Carroll et al., J. Med. Chem., 19, pp. 1111–1118, (1976).

Primary Examiner—Glennon H. Hollrah
Assistant Examiner—D. B. Springer
Attorney, Agent, or Firm—John H. Raubitschek; John M. Petruncio; Werten F. W. Bellamy

[57] ABSTRACT

Improved means for the chemotherapy of malaria have been achieved with 5-alkoxy-primaquine analogues having the formula:

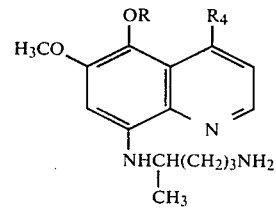

wherein $R_4$ represents hydrogen or a methyl grouping, and R represents an alkyl group containing 3 to 12 carbon atoms and pharmaceutically acceptable salts thereof, wherein the salt-forming acid may be organic or inorganic in nature. These primaquine-related compounds afford improvement in the chemotherapy of malaria by exerting plasmodicidal action on malaria parasites which may be present in either the blood, formed tissues, or blood and formed tissues of the mammalian host. Such broad and practical spectrum of effectiveness distinguishes the said primaquine analogues, which may be administered parenterally or perorally to infected animals.

28 Claims, No Drawings

5-(STRAIGHT CHAIN 3–12 CARBON ALKOXY)-8-QUINOLINAMINES AND THEIR USE FOR TREATMENT OF MALARIA

The invention described herein may be manufactured and used by or for the Government, for governmental purposes, without the payment of any royalties thereon or therefor.

This application is a continuation of application Ser. No. 229,487, filed Jan. 29, 1981, now abandoned.

BACKGROUND OF THE INVENTION

Malaria has long presented the most serious of global public health problems among the infectious diseases. Attempts to control the mosquito vector and use of antimalarials notwithstanding, there are yet some one million fatalities annually from the disease. Not clearly evident in the mortality statistics are the vast range of problems related to the tens of millions cases suffering from morbidity derived from malaria infections. In part, the extent of the economic and public health problems derived from malaria has been related to difficulties in the chemotherapy of that protozoan disease. The narrow spectrum of action of antimalarial drugs in relation to the life cycle of the parasite has been clearly apparent, for example. Development of drug resistance by Plasmodia has further complicated a situation which of necessity includes use of compounds which may be poorly tolerated by many individuals.

Treatment of acute malaria is an urgent medical problem, and may constitute a grave emergency lest there be fatal consequences. Acute malaria is a result of presence of Plasmodia in the bloodstream, and those parasites must be eradicated to give clinical cure. Malaria resulting from infection with *Plasmodium falciparum* frequently leads to a severe pathophysiologic cascade and death may occur soon after onset of symptoms. Elimination of blood forms of the parasite ordinarily clears the body of *Plasmodium falciparum* (clinical cure of malaria). Infection with *Plasmodium vivax* (and also the rarer parasites, *Plasmodium malariae* and *Plasmodium ovale*, to variable extent) gives rise to a considerable reservoir of tissue forms (exoerythrocytic stage) of the parasite which are able to cause relapses of malaria through intermittent reinvasion of the blood, as, following treatment of the original attack. Thus, alleviation of acute vivax malaria with a (clinical) curative drug does not perforce achieve elimination of all parasites from the body and produce a radical cure. Only when all of the organisms have been cleared from blood and formed tissues can there be freedom from possible relapse of the malaria. Mixed infections in people, as with *Plasmodium falciparum* and *Plasmodium vivax*, require treatment including both clinically curative and radical curative drugs to afford actual eradication of the malaria.

In clinical practice, the management of acute malaria may well follow differing patterns, depending upon the parasite and the severity of the infection. When acquired in regions where falciparum malaria is responsive to chloroquine, that drug or other 4-aminoquinoline may be used in oral treatment of the condition. If the falciparum parasites may be resistant to chloroquine, or if obviously severe infection is presented, treatment may well be by an intravenous infusion of quinine followed by oral administration of mefloquine or of pyrimethamine-sulfadoxine combination. Acute vivax malaria (or, malariae malaria, or ovale malaria) ordinarily responds well to chloroquine treatment. Prevention of relapses due to persistent tissue forms of *Plasmodium vivax* (and, *Plasmodium malariae*, or *Plasmodium ovale*) requires use of a radically curative agent. Presently, only primaquine serves as a clinically effective radically curative antimalarial drug. It clears the tissues of malaria parasites (i.e., tissue schizonticide) and also kills sexually differentiated forms (gametocytes) in the blood at clinically usable doses. On the other hand, primaquine is relatively ineffective against the blood schizonts (i.e., little of blood schizonticidal action) which evoke clinical symptoms of malaria. The toxicity of primaquine precludes administration of doses which would afford worth in overt cases of malaria, for it must even be given in divided doses over some 14 days to achieve radical curative effects in humans.

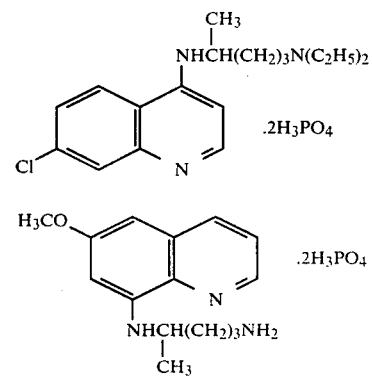

It has become apparent that palliative effects of chloroquine are achieved with safe doses of the drug, whereas primaquine may give evidence of toxic effects even at therapeutic doses [cf. World Health Organization report WHO/MAL/79.905 (1979), H. Weniger]. Thus, chloroquine must be administered to scavenge schizonts from the blood while primaquine destroys tissue forms. It appears that the problem with use of primaquine for both effects is two-fold, viz., inadequate blood schizonticidal activity and undue toxicity.

In the course of the U.S. program on antimalarials research during 1941–1945, the serious attempts made to improve the profile of pamaquine led to primaquine. Some investigations of 8-aminoquinolines were continued toward broadening the effectiveness and decreasing the toxicity of primaquine. One approach was to alter the basic side-chain. A representative was 6-methoxy-8-(5-propylaminopentylamino)quinoline phosphate [U.S. Pat. No. 3,096,334 (2 July 1963) E. A. Steck; J. Org. Chem., 24, 700 (1959) E. A. Steck with L. T. Fletcher], which had sufficiently good profile as a blood- and tissue-schizonticide in the laboratory [Antibiotics Chemother., 12, 103 (1962) D. A. Berberian, et al.] that it underwent field trials [e.g., Bull. W. H. O., 32, 591 (1965) R. D. Powell]. It became apparent that such structural modification achieved no appreciable improvement in over-all worth of primaquine. Other approaches toward enhancing effectiveness of primaquine included synthesis of 4-methyl primaquine [J. Am. Chem. Soc., 77, 4816 (1955), R. C. Elderfield, et al.]. Although previous test systems failed to identify it as superior to primaquine, recent improvements in the evaluation of antimalarials [cf., Am. J. Trop. Med. Hyg., 24, 174 (1975), K. E. Kinnamon and W. E. Rothe; ibid., 27, 718 (1978), L. H. Schmidt; ibid., 28, 937 (1979), D. S. Rane and K. E. Kinnamon] so indicated. Note may also be taken of the synthesis of 5-substituted 8-aminoquinoline derivatives during the World War II program of antimalarial research in the U.S.A.:-cf. The Chemotherapy of Protozoan Diseases, by E. A. Steck (published 1972 by Walter Reed Army Institute of Research, Washington, D.C.)—volume 3, pages 23.160 to 23.162.

SUMMARY OF THE INVENTION

The present invention relates to novel improvements in the chemotherapy of malaria, consisting in the development of new primaquine analogues which exhibit practical levels of effectiveness in experimental malaria both when induced by sporozoites of infectious Plasmodia and by introduction of infectious trophozoites of the parasites. Such range of chemotherapeutic effectiveness against forms of the malaria parasite both in tissues and in blood affords a unique melding of worth especially because achieved without the gross liability of hazardous toxic side-effects otherwise characteristic of 8-aminoquinolines. In truth, such new primaquine analogues provide a remarkably broad spectrum of antimalarial activity in relation to the life cycle of the parasite. Practical utility of the class as being both clinically curative and radically curative antimalarials is envisioned.

DETAILED DESCRIPTION OF THE INVENTION

Currently employed antimalarials suffer disadvantages in use, owing to relatively circumscribed spectrum of action in relation to the life cycle of the malaria parasite. Herewith there have been developed 8-quinolinamines which have demonstrated a broad range of effectiveness against forms of Plasmodia resident in blood and in formed tissues of infected mammals. Subject compounds are 5-alkoxy analogues of primaquine and of 4-methylprimaquine which may be administered parenterally or perorally to achieve the desired therapeutic effects. For convenience, subject drugs may be administered in the form of the neat chemical bases or as salt of a pharmaceutically acceptable acid, either inorganic or organic in chemical nature. Non-restrictive examples of inorganic acids suitable for preparation of salts of (I) include: hydrochloric acid; phosphoric acid; nitric acid; sulfamic acid; and sulfuric acid. Suitable organic acids which may be used to form salts of (I) include the following, nonrestrictive examples: maleic acid; fumaric acid; citric acid; beta resorcylic acid; and pamoic acid.

When administered in oral dosage forms, subject antimalarial agents may be incorporated into tablets (single or multi-layer, coated or uncoated), capsules, dragees, and the like. The formulation of such oral dosage forms may advantageously include optional excipients such as lactose, precipitated chalk, dibasic calcium phosphate, microcrystalline cellulose derivatives, maize starch, talc, calcium stearate, or like adjuvant substances whose identity and use are well known in pharmaceutical compounding art. For parenteral administration, aqueous or oily solutions of these lepidine derivatives may be used in a wide range of concentrations. In certain instances, advantage may be gained with use of aqueous suspensions such as may be obtained with ethoxylated sorbitan fatty acid esters, optionally with addition of thickeners such as carboxymethyl cellulose or polyethylene glycol.

The requisite primaquine analogues were made from an appropriate 5-OR-8-amino-6-methoxyquinoline by the method described in U.S. Pat. No. 4,167,638 issued Sept. 11, 1979 to E. H. Chen, A. J. Saggiomo, and E. A. Nodiff which is incorporated herein by reference. The 5-OR-8-amino-6-methoxyquinoline proceeded via an intermediate phthalimide derivative, which was cleaved (hydrazine) to provide the target compound. Synthesis of the 8-amino compound was accomplished by reduction of the corresponding 5-OR-6-methoxy-8-nitroquinoline.

With the exception of the 5-OCH$_2$CH$_3$ and 5-OCH$_2$CF$_3$ derivatives, all 5-OR-6-methoxy-8-nitroquinolines wherein R represents alkyl and R$_4$ represents CH$_3$ or H were made from the 5-hydroxy-6-methoxy-8-nitroquinolines and RX in the presence of base. The exceptions were obtained from 5-halo-6-methoxy-8-nitroquinolines and ROH.

EXAMPLES

Herein are offered examples which provide methods for illustrating, without implied limitations the practice of this invention for novel treatment of malaria infections with 8-amino-6-methoxyquinolines which exert clinically curative and radically curative antimalarial activity.

All temperatures not otherwise indicated are in degrees Celsius (°C.). All parts or percentages are given by weight.

METHODS

Malaria parasites (Plasmodia) are well-known to have complex life cycles: cf. Malaria Parasites and Other Haemosporidia, by P. C. C. Garnham (Blackwell Scientific Publications, Oxford, 1966). For such reason, various procedures have been developed to assess antimalarial effects at specified stages in the life cycle (Kinnamon and Rothe; Schmidt; Rane and Kinnamon, locc, cit.). In the evaluation of compounds developed in instant program, testing was done for blood schizonticidal effects in mice and for tissue schizonticidal action in rhesus monkeys. Each test system had been standardized, so that clear and reproducible definition of effectiveness could be obtained.

Blood Schizonticidal Test (Trophozoite-Induced *Plasmodium berghei* Infection in Mice)

This system is based on comparisons of responses to test compounds by *Plasmodium berghei* KBG 173 malaria in mice as expressed in mean survival times and the mean survival times of untreated controls. Thus, compounds noted as active produce increases in the survival times of the treated animals that are significant when compared with the survival times of untreated controls. Since an established disease is less sensitive to treatment than a disease in the early stages of development, treatment is withheld until the parasitemia is relatively high in order to insure a more reliable assay of activity and the selection of appropriate compounds for intensive pre-clinical studies.

Utilizing young ICR/HA Swiss mice and a standard inoculum of *Plasmodium berghei* KBG 173, it is possible to produce a uniform disease fatal to 100% of untreated animals within 6 to 8 days with a mean survival time of 6.2 days. Test animals weigh from 18 to 22 grams but weight variations in any given experimental or control group are confined to 2–3 grams. All animals in any given test are approximately of the same age. Animals on test are housed in metal-topped plastic cages, given a standard laboratory diet and water ad libitum.

Test animals receive an intraperitoneal injection of 0.5 ml of 1:100 dilution of heparinized heart's blood with a minimum of 90% parasitized cells ($4 \times 10^7$ cells), drawn from donor mice infected one week earlier with *Plasmodium berghei*. The donor strain is maintained by weekly passages in separate groups of mice inoculated with a 0.5 ml of 1:500 dilution of heparinized heart's blood.

Test compounds are administered after dissolution or suspension in peanut oil. A single dose is given subcutaneously 72 hours after the mice are infected with *Plasmodium berghei*. At this time a 10–15 percent parasitemia has developed; the disease is well established but has not produced sufficient debility to alter the response of the host to toxic effects of the drug on test. Since treatment is withheld for three days to permit the infection to become well established and death occurs in untreated controls within 6–8 days, it is felt that this system presents a candidate compound with the maximum challenge. In order to check factors such as changes in the infectivity of *Plasmodium berghei* or in the susceptibility of the host or to detect technical errors, a group of infected animals treated with pyrimethamine at dose levels producing definite increases in survival time is included as a positive control in every experiment.

In each experiment test compounds are administered in graded dosages. With highly active compounds, increases in dose levels are usually followed by increases in the survival time of the treated mice. However, if an active drug is toxic for the host, its toxicity may become a limiting factor; continued increases in dose levels also increase the toxic effects and may result in the diminution of survival times. Deaths prior to the sixth day, when untreated controls begin to die, are regarded as nonparasitic and become the basis for toxicity evaluations. Treated animals are kept under observation for 60 days. Survivors at the end of this period of time are considered as cured.

An increase of 100% in mean survival time is considered the minimum effective response for a candidate compound. In calculating mean survival time, toxic deaths and 60 day survivors are not included.

Tissue Schizonticidal Test (Sporozoite-Induced *Plasmodium cynomolgi* Infection in Rhesus Monkeys)

This test is designed to evaluate the tissue schizonticidal (radical curative) activity of test compounds. Well-conditioned Indian rhesus monkeys of either sex weighing 2-4 Kg are utilized. *Plasmodium cynomolgi* (strain B) sporozoites are prepared by grinding heavily infected Anopheles balabacensis salivary glands in 1:1 monkey serum-saline vehicle.

Monkeys are infected by I.V. injection of $10^6$ freshly isolated *Plasmodium cynomolgi* sporozoites on day 0. A rapidly rising parasitemia developed after a 7–9 day prepatent period, and administration of the test drug is initiated when the rising parasite count exceeds 5000 per mm$^3$ (typically day 10-12). Test drugs are normally administered orally (by nasogastric intubation) once daily for 7 consecutive days in aqueous solution or, if insoluble, in suspension in 0.3% methylcellulose solution. Chloroquine diphosphate (3.1 mg/kg base/kg orally per day) is *always* administered concurrently with the test drug for 7 days to eliminate blood schizonts. Thus, any tissue schizonticidal activity of the test drug will always be apparent even if it lacks blood schizonticidal activity.

A vehicle control monkey and a positive drug control (primaquine) monkey are included in each group of inoculated monkeys.

The effect of the test drug is determined by counting blood parasites. Parasite counts are made daily through day 20, and every two days thereafter. Initially a clearance of blood parasites is observed due to the blood schizonticidal action of chloroquine. If exoerythrocytic parasites ("tissue schizonts") survive the action of the test drug (i.e. if the drug is inactive or incompletely active) there will be a "relapse" of blood parasites. If there is no relapse within 20 days of the initial clearance of parasitemia, the monkey is splenectomized and its parasitemia followed for an additional 30 days. If there is no relapse within this period, the experiment is terminated and the monkey is considered "cured."

Primaquine diphosphate cures 90% of monkeys in this test system when administered at a dose of 1.3 mg/kg per day for 7 days (1.0 mg/kg free base) in combination with chloroquine.

RESULTS

Appended tables provide summary on the antimalarial testing of the 8-quinolinamines. Primaquine and 4-methyl primaquine are given in Table 1 and the series of 5-substituted primaquine analogues herein disclosed are in Tables 2 and 3. It should be noted that blood schizonticidal testing of compounds would ordinarily use chloroquine, a 4-aminoquinoline, as a standard; here, primaquine has been included by way of comparison to show its poor level of effectiveness in such regard. Quite properly, primaquine provides firm basis for assessment of worth in tissue schizonticidal testing.

EXAMPLE 1

5-ETHOXYPRIMAQUINE

A. 5-Chloro-6-methoxy-8-nitroquinoline

To 150 ml of phosphorus oxychloride, at an internal temperature of 80°–85°, was added in portions, with vigorous stirring, during 0.5 hr, 40.5 g (0.184 mole) of 5-hydroxy-6-methoxy-8-nitroquinoline. After completion of addition, the mixture, which had turned from a red solution to a yellow suspension, was heated under reflux for 1.5 hr. The golden yellow solution was allowed to cool to room temperature and the resulting yellow mush was added to a vigorously stirred mixture of 700 ml of conc ammonium hydroxide and ice. The addition rate was regulated to keep the temperature from rising above 25° The pale yellow precipitate was washed with water and air dried to give 43 g (97%) of 5-chloro-6-methoxy-8-nitroquinoline mp 204°–206° (Mp 204° cited by R. C. Fuson et al., J. Org. Chem., 12, 799 (1947).

B. 5-Ethoxy-6-methoxy-8-nitroquinoline

To a stirred, refluxing solution of 3.63 g (0.055 mole) of 85% potassium hydroxide in 500 ml of ethanol was added 12 g (0.05 mole) of 5-chloro-6-methoxy-8-nitroquinoline. The heat was removed, 5.5 g (0.055 mole) of triethylamine was added and the resulting tan suspension was heated under reflux for 12 hr. The mixture, which was now a brown solution, was cooled and 0.6 g of starting material was removed by filtration. The filtrate was taken to dryness in vacuo and the residue was washed with water to give 12 g of crude product as brown crystals, mp 88°–95°. Recrystallization from ligroin (bp 90°–120°) (carbon) provided 10 g (80%) of yellow crystals, mp 98°–99.5°.

Anal. Calcd. for $C_{12}H_{12}N_2O_4$: C, 58.06; H, 4.87; N, 11.29. Found: C, 57.87; H, 4.68; N, 11.11.

The water washings of the crude 5-ethoxy-6-methoxy-8-nitroquinoline were acidified with acetic acid and basified with sodium bicarbonate to give 0.44 g of 5-hydroxy-6-methoxy-8-nitroquinoline.

C. 8-Amino-5-ethoxy-6-methoxyquinoline.

A mixture of 8.1 g (0.033 mole) of above nitro compound, 0.2 g of platinum oxide and 200 ml of ethanol was shaken in a Parr apparatus at room temperature for 2 hr under 65 psig of $H_2$. The mixture was vented, flushed with $N_2$, treated with carbon and a pinch of sodium dithionite and filtered. The filtrate was brought to dryness in vacuo and the brown solid residue was dissolved in 400 ml of boiling ligroine (bp 90°–120°). The solution was treated with carbon and a pinch of sodium dithionite and filtered. The filtrate was concentrated to 200 ml (brown solution) and cooled to yield 5.1 g (71%) of 8-amino-5-ethoxy-6-methoxyquinoline, mp 129°–131°. Recrystallization from ligroine provided an analytical sample as yellow crystals, mp 132.5°–133.5°.

Anal. Calcd. for $C_{12}H_{14}N_2O_2$: C, 66.03; H, 6.47; N, 12.84. Found: C, 66.28; H, 6.31; N, 12.64.

D. 5-Ethoxy-6-methoxy-8-(1-methyl-4-phthalimidobutylamino)quinoline

A stirred mixture of the foregoing amino compound (8.4 g, 0.0384 mole) and 4-bromo-1-phthalimidopentane (14.4 g, 0.048 mole) was heated at 150°–155° while triethylamine (5.6 g, 0.056 mole) was added in portions during 2 hr. The very dark mixture was continued at 150° for 4 hr and allowed to cool overnight. It was re-heated to 150°, treated with more 4-bromo-1-phthalimidopentane (14.4 g), in a single portion, and with triethylamine (5.6 g), portionwise during 2 hr, and then allowed to stir at 150° for 2 additional hr. The latter addition sequence was repeated three more times, the mixture was allowed to cool, diluted with acetone (300 ml) and filtered to yield (after washing with acetone) 30.2 g (99%) of triethylamine hydrobromide. The filtrate was concentrated under vacuum and the residual mush was triturated with 400 ml of warm diethyl ether. A dark brown solid (2.7 g) was filtered (discarded) and the filtrate was dried (Drierite) and treated with carbon (2X). The orange-brown solution was treated with excess ethereal hydrochloric acid and the resulting red-orange precipitate was allowed to coagulate and then washed repeatedly with diethyl ether. The tacky red-brown solid was basified with 10% ammonium hydroxide and the yellow mixture was extracted with chloroform (2×300 ml). The combined extracts were dried (Drierite), treated with carbon and taken to dryness in vacuo. The remaining brown-orange gum (13.5 g, 77%) was used in the next step without further purification. Tlc of this material (silica, chloroform, $I_2$ visualization) revealed a single spot.

E. 8-(4-Amino-1-methylbutylamino)-5-ethoxy-6-methoxyquinoline Fumarate

An orange-brown solution of 13.5 g (0.031 mole) of the intermediate phthalimido compound, 657 ml of ethanol, 387 ml of chloroform and 20 ml of 95% hydrazine was heated under reflux for 6 hr, allowed to cool overnight, and filtered to remove 4.9 g (after washing with ethanol and chloroform) of phthalhydrazide (97% of theory). The orange-brown filtrate was evaporated in vacuo and the residual mush was treated with 800 ml of diethyl ether. The mixture was extracted with 30% potassium hydroxide (2×250 ml), water (3×100 ml), dried (Drierite), treated with carbon and filtered. The yellow filtrate was concentrated, under reduced pressure, to 500 ml and the stirred concentrate was treated, portionwise, with a hot solution of 3.65 g (0.031 mole) of fumaric acid in 100 ml of isopropyl alcohol. The thick yellow precipitate was filtered, washed with cold isopropyl alcohol and diethyl ether and vacuum-dried to give 7.9 g (60%) of 5-ethoxy primaquine fumarate as an orange solid, mp 155°–157°. Crystallization from isopropyl alcohol (carbon) provided 6.3 g of golden yellow solid, mp 154°–156°.

Anal. Calcd. for $C_{21}H_{29}N_3O_6$: C, 60.13; H, 6.97; N, 10.02. Found: C, 60.25; H, 6.97; N, 9.82.

EXAMPLE 2

5-(2,2,2-TRIFLUOROETHOXY)PRIMAQUINE

A. 6-Methoxy-8-nitro-5-(2,2,2-trifluoroethoxy)quinoline

To a solution of 0.5 g (0.02 g atom) of sodium in 30 ml of 2,2,2-trifluoroethanol were added 5.6 g (0.02 mole) of 5-bromo-6-methoxy-8-nitroquinoline and 7 ml of pyridine. The mixture was heated under reflux for 158 hr and filtered to remove 1.3 g of starting material. The filtrate was concentrated to 50 ml, diluted with diethyl ether, washed with water and dried (potassium carbonate). Solvent removal left a tan crystalline powder, mp 109°–115° which was extracted with benzene. (A trace of insoluble red crystals was discarded.) The benzene solution was concentrated and the resulting residue was crystallized from diethyl ether-petroleum ether (20°–40°) (5:1) to give 0.4 g of pale tan crystals of 6-methoxy-8-nitro-5-(2,2,2-trifluoroethoxy)quinoline, mp 117°–119°. Concentration of the mother liquor provided an additional 2 g of product, mp 100°–111°. Crystallization of the first fraction from diethyl ether and vacuum drying, overnight, at 60°, gave the analytical sample, mp 120°–121°.

Anal. Calcd. for $C_{12}H_9F_3N_2O_4$: C, 47.69; H, 3.00; F, 18.86. Found: C, 47.96; H, 2.89; F, 18.55.

B. 8-Amino-6-methoxy-5-(2,2,2-trifluoroethoxy)quinoline

A mixture of 5 g (0.016 mole) of the foregoing nitro compound, 5 g of iron filings, 100 ml of water and 1 ml of acetic acid was stirred at 120° for 6 hr, cooled and filtered. The residue and the filtrate were extracted with diethyl ether and the combined, dried (magnesium sulfate) extracts were concentrated to give yellow-green crystals. Solution in chloroform and passage through a silica column gave yellow crystals, mp 91°–94°, whose melting point was raised to 94°–97° by crystallization from diethyl ether, yield 3.4 g (76%). Washing with petroleum ether (bp 20°–40°) afforded an analytical sample of 8-amino-6-methoxy-5-(2,2,2-trifluoroethoxy)quinoline as fine, white needles, mp 95°–96°.

Anal. Calcd. for $C_{12}H_{11}F_3N_2O_2$: C, 52.95; H, 4.07; N, 10.29. Found: C, 53.08; H, 4.06; N, 10.03.

C. 6-Methoxy-8-(1-methyl-4-phthalimidobutylamino)-5-(2,2,2-trifluoroethoxy)quinoline Hydrochloride Hemihydrate A stirred mixture of 3 g (0.011 mole) of the above amino compound and 3 g (0.01 mole) of 4-bromo-1-phthalimidopentane was maintained at 120° while 1.5 ml of triethylamine was added dropwise during 0.5 hr. The temperature was continued at 120° while increments of 4-bromo-1-phthalimidopentane (3 g) and triethylamine (1.5 ml) were added three times, at 1.5 hr intervals, in the usual manner. The mixture was allowed to cool, diluted with acetone and filtered. The filtrate was concentrated in vacuo and the residue was dissolved in diethyl ether, washed with 20% potassium hydroxide and extracted with 20% hydrochloric acid. Within minutes, red-orange crystals separated from the extract. Washing of the crystals with diethyl ether-ethanol (5:1), gave 3.9 g (66%) of the phthalimido intermediate, mp 152°–154°. Crystallization from ethanol did not change the melting point.

Anal. Calcd. for $C_{25}H_{26}ClF_3N_2O_{1.5}$: C, 56.34; H, 4.92; N, 7.89. Found: C, 56.80; H, 5.07; N, 7.73.

D. 8-(4-Amino-1-methylbutylamino)-6-methoxy-5-(2,2,2-trifluoroethoxy)quinoline Fumarate Hemihydrate A stirred mixture of 2 g (0.0037 mole) of the above phthalimide derivative, 50 ml of chloroform, 150 ml of ethanol and 15 ml of 95% hydrazine was heated under reflux for 6 hr, allowed to cool and filtered. The filtrate was concentrated to a syrup, dissolved in diethyl ether, washed with 30% potassium hydroxide and extracted with 20% hydrochloric acid. The extract was washed with diethyl ether, basified with 30% potassium hydroxide and extracted with diethyl ether. After washing (water) and drying (sodium sulfate) the ethereal solution was treated with 2% fumaric acid in 2-propanol to give 0.6 g of crude fumarate, mp 145°–170°. Crystallization from 2-propanol containing a small amount of fumaric acid provided 0.3 g of the target compound, in the form of its fumarate salt, mp 169°–171°.

Anal. Calcd. for $C_{21}H_{27}F_3N_3O_{6.5}$: C, 52.29; H, 5.64; N, 8.71. Found: C, 52.41; H, 5.43; N, 8.87.

EXAMPLE 3

5-(n-PROPOXY)PRIMAQUINE

A. 6-Methoxy-8-nitro-5-(n-propoxy)quinoline

To a stirred mixture of 15 g (0.068 mole) of 5-hydroxy-6-methoxy-8-nitroquinoline, 16.8 g (0.14 mole) of n-propyl bromide, 1.5 g of triethylamine and 20 g of hexamethylphosphoric triamide, heated at a bath temperature of 110°, was added dropwise, during 2 hr, 20 g of propylene oxide. After an additional 48 hr at 110° the green-brown mixture was poured into 150 ml of water. The aqueous mixture was extracted with diethyl ether and the extract was dried (magnesium sulfate) and concentrated to give a dark yellow residue. Crystallization from hexane provided 11.1 grams (62%) of 6-methoxy-8-nitro-5-(n-propoxy)quinoline as yellow crystals, mp 100°–104°. Recrystallization from methanol gave an analytical sample as pale yellow crystals, mp 101°–103°.

Anal. Calcd. for $C_{13}H_{14}N_2O_4$: C, 59.53; H, 5.39; N, 10.68. Found: C, 59.62; H, 5.28; N, 10.67.

B. 8-Amino-6-methoxy-5-(n-propoxy)quinoline

A mixture of 5.5 g (0.02 mole) of the foregoing nitroquinoline, 5 g of iron filings, 200 ml of water and 3 ml of acetic acid was heated at 90°–95° for 24 hr, cooled and filtered. The filter cake was extracted with hot hexane (3×200 ml) and the combined extracts were dried (magnesium sulfate), treated with Darco G-60 and concentrated to give 3.5 g (72%) of 8-amino-6-methoxy-5-(n-propoxy)quinoline as yellow needles, mp 73°–74°.

Anal. Calcd. for $C_{13}H_{16}N_2O_2$: C, 67.22; H, 6.94; N, 12.06. Found: C, 67.25; H, 6.78; N, 12.01.

C. 6-Methoxy-8-(1-methyl-4-phthalimidobutylamino)-5-(n-propoxy)quinoline

A mixture of 2 g (0.0086 mole) of the above amino compound and 2.5 g of 4-bromo-1-phthalimidopentane was heated in an oil bath at 140° while 1.3 g of triethylamine was added dropwise during 0.5 hr. Heating was then continued for two more hours. Additional quantities of the bromo compound (2.5 g) and triethylamine (1.3 g) were added twice more in the usual manner. The reaction mixture was allowed to cool, diluted with 100 ml of acetone, stirred for 15 min and filtered. The filtrate was concentrated to a brown paste, dissolved in 50 ml of chloroform and passed through a silica gel column. The eluate was concentrated and the yellow oil was distilled to remove the fraction boiling below 140° at 0.15 mm. The residue was redissolved in chloroform and again passed through a silica gel column. After concentration of the yellow eluate, the resulting yellow oil was triturated with diethyl ether-petroleum ether (bp 20°–40°) to give 6-methoxy-8-(1-methyl-4-phthalimidobutylamino)-5-(n-propoxy)quinoline as tan crystals, mp 140°–143°. This material was recrystallized from hexane to give a solid, mp 145°–146°, which was used without analysis.

D. 8-(4-Amino-1-methylbutylamino)-6-methoxy-5-(n-propoxy)quinoline Fumarate A stirred mixture of 10 g of intermediate phthalimido compound, 100 ml of chloroform, 800 ml of ethanol and 25 ml of 95% hydrazine was heated under reflux for 4 hr and allowed to cool. Phthalhydrazide was filtered and the filtrate was concentrated to dryness in vacuo. The residue was dissolved in 800 ml of diethyl ether, washed with 30% potassium hydroxide and extracted with 20% hydrochloric acid. The red extract was washed with diethyl ether, cooled and basified with 30% potassium hydroxide. The red oil was extracted with diethyl ether, and the extract was dried (potassium carbonate) and treated with 1% ethanolic fumaric acid. The resulting solid was crystallized from acetone-methanol (5:1) to give 2.7 g of the desired compound as yellow crystals, mp 165–166.

Anal. Calcd. for $C_{22}H_{31}N_3O_6$: C, 60.96; H, 7.21; N, 9.69. Found: C, 60.78; H, 7.19; N, 9.61.

Concentration of the mother liquor produced an additional 2.1 g of fumarate, mp 164°–166°, for a total yield of 4.8 g (49%).

EXAMPLE 4

5-(n-BUTOXY)PRIMAQUINE

A. 5-(n-Butoxy)-6-methoxy-8-nitroquinoline

To a stirred mixture of 5-hydroxy-6-methoxy-8-nitroquinoline (15.4 g, 0.07 mole), n-butyl bromide (19.2 g, 0.14 mole), triethylamine (0.5 g) and hexamethylphosphoric triamide (6 ml), heated at 120°–130°, was added, during 2 hr, 8 g of propylene oxide. Heating was maintained at 130°–140° for 2 hr, an additional 8 ml of hexamethylphosphoric triamide was added and heating was continued at gentle reflux overnight. A low-boiling fraction was distilled off at 100° (1 atm.) and the residue was poured into 1 liter of water. The mixture was filtered and the slightly gummy tan solid was triturated with petroleum ether (bp 20°–40°) to give a tan powder. This material was dissolved in diethyl ether, washed with dilute sodium hydroxide and water and dried (sodium sulfate). Evaporation of the solvent left a tan solid which on crystallization (methanol) provided 13.5 g (70%) of 5-butoxy compound as pale yellow solid, mp 70°–72°. An additional crystallization from methanol gave the analytical sample as short yellow needles, mp 71°–73°.

Anal. Calcd. for $C_{14}H_{16}N_2O_4$: C, 60.85; H, 5.84; N, 10.14. Found: C, 61.08; H, 5.72; N, 9.87.

B. 8-Amino-5-(n-butoxy)-6-methoxyquinoline

A stirred mixture of 5-butoxy-6-methoxy-8-nitroquinoline (11.2 g, 0.04 mole), degreased 40 mesh iron filings (12 g), water (100 ml), acetic acid (2.5 ml) and butyl ether (3 ml) was heated at 100°–110° for 3 hr, cooled and filtered. The filter cake was dried and extracted with 4×300 ml of ligroine (bp 60°–90°). The combined extracts were treated with carbon, concentrated to 120 ml and cooled to give 8 g (82%) of amino compound as yellow crystals, mp 78°–80°. Recrystallization from ligroine (bp 60°–90°) raised the mp to 80°–81°.

Anal. Calcd. for $C_{14}H_{18}N_2O_2$: C, 68.28; H, 7.36; N, 11.38. Found: C, 68.04; H, 7.27; N, 11.14.

C. 5-(n-Butoxy)-6-methoxy-8-(1-methyl-4-phthalimidobutylamino)quinoline

A stirred mixture of the foregoing aminoquinoline derivative (5.5 g, 0.022 mole) and 4-bromo-1-phthalimidopentane (10 g, 0.033 mole) was maintained at 150°–155° while triethylamine (3 g, 0.03 mole) was added in portions during 1.5 hr. Heating was continued for 2 more hours when an additional 7 g (0.023 mole) of 4-bromo-1-phthalimidopentane was added in one portion followed by 2.2 g (0.022 mole) of triethylamine during 2 hr. After 2 more hours at 150°–155°, tlc indicated the absence of the amino compound. The mixture was allowed to cool and diluted with acetone. The resulting triethylamine hydrobromide was filtered and the filtrate was treated with carbon and concentrated. The residue was extracted with diethyl ether and the filtered extract was treated stepwise with ethereal hydrochloric acid. The first small dark fraction was discarded. Continued treatment of the clear, red filtrate with diethyl ether-hydrochloric acid gave a pale red-brown gummy solid. This solid was basified with ammonium hydroxide and extracted with diethyl ether. The extract was dried (sodium sulfate) and concentrated to give 8 g (87%) of the intermediate phthalimide type as a pale brown oil which was used without further purification.

D. 8-(4-Amino-1-methylbutylamino)-5-(n-butoxy)-6-methoxyquinoline Fumarate

A stirred mixture of the foregoing intermediate phthalimide derivative (10 g, 0.022 mole), 95% hydrazine (16 ml) and ethanol (300 ml) was heated under reflux for 4 hr and allowed to cool. Phthalhydrazide (4.5 g) was filtered and the filtrate was brought to dryness in vacuo. The residue was extracted with diethyl ether and the filtered extract was washed with 30% potassium hydroxide (3×100 ml) and water (4×50 ml) and dried (magnesium sulfate). The extract was treated with 1% fumaric acid in isopropanol to give 4 g of the above-named target, mp 152°–153°. Concentration of the mother liquor provided an additional 1.5 g for a total yield of 5.5 g (62%). Two crystallizations from acetone provided 3.5 g of fumarate as a yellow solid, mp 157°–159°.

Anal. Calcd. for $C_{23}H_{33}N_3O_6$: C, 61.73; H, 7.43; N, 9.39. Found: C, 61.59; H, 7.23; N, 9.19.

EXAMPLE 5

5-(n-PENTOXY)-4-METHYLPRIMAQUINE

A. 6-Methoxy-4-methyl-8-nitro-5-pentoxyquinoline

A stirred mixture of 7.8 g (0.032 mole) of 5-hydroxy-6-methoxy-4-methyl-8-nitroquinoline, 2.5 g (0.016 mole) of 1-bromopentane and 8 ml of hexamethylphosphoric triamide was maintained at 120°, under $N_2$, while a mixture of triethylamine (1 ml) and propylene oxide (6 ml) was added in small portions during 6 hr. The reaction was continued for 2 hr, allowed to cool and filtered. The dull red solid was washed with acetone and water and dried to give 3.5 g of starting material. The combined filtrate and washings were treated with carbon and evaporated to a viscous oil. After thorough trituration with water, the oil turned to a dark semi-solid. The latter was extracted with diethyl ether and the extract was concentrated to a syrup. Two crystallizations from ligroine (bp 60°–90°) gave 2 g (43%) of 6-methoxy-4-methyl-8-nitro-5-(n-pentoxy)quinoline, mp 54°–55°. An additional crystallization from ligroine provided the analytical sample as pale yellow crystals, mp 56°–57°.

Anal. Calcd. for $C_{16}H_{20}N_2O_4$: C, 63.15; H, 6.62; N, 9.20. Found: C, 63.37; H, 6.66; N, 9.02.

B. 8-Amino-6-methoxy-4-methyl-5-pentoxyquinoline

A stirred mixture of nitro body, from A (2.4 g, 0.008 mole), degreased 40 mesh iron filings (6 g), water (20 ml) acetic acid (3 ml) and dibutyl ether (3 ml) was heated at 100° for 2 hr, cooled and filtered. The dark, dried solid was extracted with diethyl ether (300 ml) and the extract was evaporated to dryness. The resulting dull green solid was crystallized from ligroine (carbon) to give 1.8 g (85%) of the requisite 8-amino compound, mp 65°–66°. An additional crystallization from ligroine (bp 60°–90°) did not change the melting point.

Anal. Calcd. for $C_{16}H_{22}N_2O_2$: C, 70.04; H, 8.08; N, 10.21. Found: C, 70.19; H, 8.02; N, 9.98.

C. 6-Methoxy-4-methyl-8-(1-methyl-4-phthalimidobutylamino)-5-(n-pentoxy)quinoline A stirred mixture of 8-amino-6-methoxy-4-methyl-5-(n-pentoxy)quinoline (5.5 g, 0.02 mole) and 12 g of 4-bromo-1-phthalimidopentane was maintained at 140°–145° while triethylamine (6 ml) was added in small portions during 2 hr. Three more increments of 4-bromo-1-phthalimidopentane (3 g) and triethylamine (1 ml) were added at 2 hr intervals in the usual manner. The mixture was allowed to cool and extracted with diethyl ether (ca. 500 ml). The filtered extract was treated with carbon and concentrated to leave a brown oil. Solution in diethyl ether and treatment with ethereal hydrochloric acid produced a red oil. The oil was dissolved in 300 ml of chloroform, basified with dilute sodium hydroxide, washed with water, dried (postassium carbonate) and concentrated to give 9 g (93%) of requisite phthalimido compound as a brown oil. This material was used without further purification.

D. 8(4-Amino-1-methylbutylamino)-6-methoxy-4-methyl-5-(n-pentoxy)quinoline Fumarate A stirred mixture of the phthalimide type from C (6.6 g, 0.014 mole), 95% hydrazine (8 ml) and ethanol (300 ml) was heated under reflux for 45 min. Chloroform (50 ml) was added and a precipitate of phthalhydrazide formed almost immediately. Reflux was continued for an additional 75 min and the mixture was cooled, filtered and concentrated in vacuo. The residue was extracted with diethyl ether and the filtered extract was washed with 30% potassium hydroxide (4×50 ml) and water and dried (sodium sulfate). The dry extract was slowly treated with diethyl ether-hydrochloric acid until the occurrence of a sudden color change from yellow to red-orange. The ethereal solution was extracted with water and the aqueous extract was basified with dilute potassium hydroxide and extracted with diethyl ether. After washing with water, the ethereal solution was dried and treated with 1% fumaric acid in acetone to give 2 g (30%) of 5-(n-pentoxy)-4-methyl-primaquine fumarate, mp 147°–153°. Several crystallizations from acetone provided an analytical sample as yellow crystals, mp 151°–153°.

Anal. Calcd. for $C_{25}H_{37}N_3O_6$: C, 63.14; H, 7.84; N, 8.83. Found: C, 63.34; H, 8.14; N, 8.98.

EXAMPLE 6

5-(n-HEXOXY)PRIMAQUINE

A. 5-(n-Hexoxy)-6-methoxy-8-nitroquinoline

A stirred mixture of 5-hydroxy-6-methoxy-8-nitroquinoline (22 g, 0.1 mole), n-hexyl bromide (18.5 g, 0.11 mole), triethylamine (1 g) and hexamethylphosphoric triamide (16 ml) was maintained at a bath temperature of 120°–130° while 10 g of propylene oxide was added during 0.5 hr. The mixture was heated at a bath temperature of 130°–145° for 3 hr and 5 more grams of propylene oxide was added. After 8 hr at 110°–120°, a low-boiling fraction was distilled off at 100° (1 atm) and the residue was cooled and poured into 3 liters of ice water. The resulting dull red solid was filtered and extracted with diethyl ether (2.5 g of 5-hydroxy compound was recovered as a diethyl ether-insoluble red solid). The ether extract was washed with dilute sodium hydroxide and water, dried (sodium sulfate) and concentrated to leave a thick oil. Trituration with petroleum ether (bp 20°–40°) gave 19.5 g (65%) of the required 5-hexoxy-quinoline derivative as a tan solid, mp 46°–49°. Crystallization from aqueous methanol (carbon) provided an analytical sample as yellow needles, mp 53°–55°.

Anal. Calcd. for $C_{16}H_{20}N_2O_4$: C, 63.15; H, 6.62; N, 9.21. Found: C, 62.86; H, 6.57; N, 9.03.

B. 8-Amino-5-(n-hexoxy)-6-methoxyquinoline

A stirred mixture of the foregoing nitro compound (17 g, 0.056 mole), degreased 40 mesh iron filings, acetic acid (4 ml), butyl ether (8 ml) and water (100 ml) was heated at 110°–120° for 6 hr, cooled and filtered. The filtrate and the filter cake were extracted with diethyl ether (100 and 400 ml, respectively) and the combined extracts were dried (sodium sulfate) and treated with ethereal hydrochloric acid to give 15.5 g (89%) of 8-amino-5-hexoxy-6-methoxyquinoline as the hydrochloride, mp 168°–171°. This material was used without additional purfication.

C. 5-(n-Hexoxy)-6-methoxy-8-(1-methyl-4-phthalimidobutylamino)quinoline

A stirred slurry of 10 g (0.032 mole) of the above aminoquinoline type, as its hydrochloride and 200 ml of diethyl ether was treated with 6 g of triethylamine. The resulting triethylamine hydrochloride (4.5 g) was filtered and the filtrate was evaporated to give the free base as a brown oil. A stirred mixture of the latter and 10.5 g (0.035 mole) of 4-bromo-1-phthalimidopentane was maintained at 150°–155° while triethylamine (4 g., 0.04 mole) was added in portions during 1.5 hr. After an additional 0.5 hr at 150°–155°, tlc indicated that much of starting quinoline was still unreacted. The reaction was allowed to stand overnight and was resumed the following day with the addition of 10.5 g of 4-bromo-1-phthalimidopentane, in a single portion, and 2 g of triethylamine during 1 hr. The mixture was treated twice more, at 2 hr intervals, with 5 g of 4-bromo-1-phthalimidopentane and 1 g of triethylamine. After two final hours at 150°–155°, tlc indicated the absence of the quinoline starting material. The mixture was allowed to cool, diluted with acetone (300 ml), treated with carbon (4 g) and filtered to remove the mixture of carbon and triethylamine hydrobromide. The filtrate was evaporated in vacuo and the residue was extracted with diethyl ether. The filtered extract was treated with excess ethereal hydrochloric acid to give a viscous oil. The supernatant was decanted and the oil was basified with dilute sodium hydroxide and extracted with diethyl ether. The extract was dried and concentrated to give 15 g (95%) of phthalimido type as a brown oil which was used without further purification.

D. 8-(4-Amino-1-methylbutylamino)-5-(n-hexoxy)-6-methoxyquinoline Furmarate

A stirred mixture of the intermediate from C, immediately above, (0.8 g), 95% hydrazine (2 ml) and ethanol (100 ml) was heated under reflux for 3 hr and allowed to cool. Phthalhydrazide was filtered and the filtrate was evaporated to dryness in vacuo. The residue was extracted with diethyl ether and the extract was washed with 30% potassium hydroxide and water and dried (sodium sulfate). The dried extract was treated with 1% isopropanolic fumaric acid to give 0.5 g of 5-hexoxyprimaquine fumarate as a yellow solid, mp 154°–156°. Two crystallizations from acetone provided the analytical sample, mp 157°–158°.

Anal. Calcd. for $C_{25}H_{37}N_3O_6$: C, 63.15; H, 7.84; N, 8.84; O, 20.19. Found: C, 63.06; H, 7.77; N, 8.75; O, 20.32.

EXAMPLE 7

5-(n-HEXOXY)-4-METHYLPRIMAQUINE

A. 5,6-Dimethoxy-4-methyl-8-nitroquinoline

To a solution of sodium metal (4.8 g, 0.2 g. atom) in methanol (300 ml) were added 50.6 g (0.2 mole) of 5-chloro-6-methoxy-4-methyl-8-nitroquinoline and 70 ml of pyridine. The mixture was stirred under reflux for 48 hr, treated with carbon and filtered hot. The residue was washed with hot methanol and the filtrate and washings were combined (total, 600 ml). On standing, 15 g of 5,6-dimethoxy-4-methyl-8-nitroquinoline, separated, mp 120°–124°. The filtrate was concentrated to 200 ml and cooled overnight to give an additional 15 g of 5,6-dimethoxy-4-methyl-8-nitroquinoline. Dilution of this filtrate with 6 liters of water provided 7 g of product for a total crude yield of 37 g. Crystallization from methanol (carbon) gave 34 g (68%) of 5,6-dimethoxy-4-methyl-8-nitroquinoline, mp 123°–125°. The same compound (m.p. and mixed m.p. 123°–125°) resulted when a Skraup reaction was performed on 4-amino-5-nitroveratrole and methyl vinyl ketone.

B. 5-Hydroxy-6-methoxy-4-methyl-8-nitroquinoline

A stirred mixture of 3.8 g (0.015 mole) of the dimethoxyquinoline from (A), 300 ml of ethanol and 3.8 ml of concentrated hydrochloric acid was heated under reflux for 18 hr, allowed to cool and filtered to give 2.7 g (76%) of the desired 5-hydroxy-6-methoxy-4-methyl-8-nitroquinoline as a red solid which decomposed without melting at ca. 260°.

C. 5-Hexoxy-6-methoxy-4-methyl-8-nitroquinoline

A stirred mixture of 5-hydroxy-6-methoxy-4-methyl-8-nitroquinoline (2.4 g, 0.01 mole), n-hexyl bromide (3.3 g, 0.02 mole), triethylamine (0.3 g) and hexamethylphosphoric triamide (2 ml) was heated at 140°–150°, under $N_2$, while propylene oxide (2 ml) was slowly added (10 min). Heating was continued for 1.5 hr and an additional ml of propylene oxide was added. The reaction was continued for 1 hr, cooled, diluted with acetone (100 ml) and filtered to remove 0.1 g of unreacted 5-OH compound. The very dark filtrate was treated with carbon and the still dark filtrate was concentrated. The residue was dissolved in diethyl ether and the ethereal solution was extracted with dilute sodium hydroxide, washed with water, dried (potassium carbonate) and treated with carbon. Removal of the solvent left a residue which, on crystallization from petroleum ether (bp 20°–40°), gave 1.8 g (57%) of 5-hexoxy compound as pale yellow crystals, mp 48°–51°. Solution in benzene, passage through a silica gel column and recrystallization from petroleum ether (bp 20°–40°) (carbon) gave the analytical sample, mp 53°–54°.

Anal. Calcd. for $C_{17}H_{22}N_2O_4$: C, 64.13; H, 6.97; N, 8.80. Found: C, 63.91; H, 6.95; N, 8.72.

D. 8-Amino-5-hexoxy-6-methoxy-4-methylquinoline

A stirred mixture of the above nitro compound (10 g, 0.03 mole), degreased 40 mesh iron filings (20 g), water (80 ml), acetic acid (10 ml) and dibutyl ether (10 ml) was heated at 100° for 6 hr, cooled and filtered. The dark, solid residue was dried and extracted with a total of 800 ml of diethyl ether. The extract was treated with carbon and the solvent was evaporated. Extraction of the residue with petroleum ether (bp 20°–40°) and cooling of the extract in Dry Ice-acetone gave 7 g of 8-amino compound. Recrystallization from ligroine (bp 60°–90°) gave 5.8 g (67%) of pure 8-amino-5-hexoxy-6-methoxy-4-methylquinoline as yellow crystals, mp 69°–71°.

Anal. Calcd. for $C_{17}H_{24}N_2O_2$: C, 70.80; H, 8.39; N, 9.72. Found: C, 70.98; H, 8.22; N, 9.57.

E. 5-Hexoxy-6-methoxy-4-methyl-8-(1-methyl-4-phthalimidobutylamino)quinoline A stirred mixture of 5.8 g (0.02 mole) of the above amino compound and 6 g (0.02 mole) of 4-bromo-1-phthalimidopentane was maintained at 140°–150° while triethylamine (3 g) was added, dropwise, during 0.5 hr. Two more increments of 4-bromo-1-phthalimidopentane (6 g) and triethylamine (3 g) were added at 1.5 hr intervals in the usual manner. The mixture was allowed to cool, diluted with acetone (100 ml) and filtered to remove triethylamine hydrobromide. The filtrate was treated with carbon and the solvent was evaporated. Extraction of the residue with diethyl ether and treatment of the filtered extract with diethyl ether-hydrochloric acid produced a red-orange semi-solid. This material was dissolved in chloroform, basified with dilute sodium hydroxide, dried (sodium sulfate) and passed through a silica gel column. Evaporation of the eluate gave 9.5 g (90%) of an oil whose infra-red spectrum was consistent with the ascribed structure. This material was used without further purification.

F. 8-(4-Amino-1-methylbutylamino)-5-hexoxy-6-methoxy-4-methylquinoline Fumarate A stirred mixture of 7.5 g (0.015 mole) of phthalimide derivative (see above), 15 ml of 95% hydrazine and 500 ml of ethanol was heated under reflux for 4.5 hr, cooled and filtered. The filtrate was evaporated to dryness, in vacuo, and the residue was extracted with diethyl ether. The filtered extract was washed with 30% potassium hydroxide (4×50 ml) and water and dried (sodium sulfate). Treatment with 80 ml of 1.5% isopropanolic fumaric acid gave 4.2 g of crude fumarate, mp 128°–135°. Crystallization from acetone (carbon) provided 3 g of the pure material, mp 147°–149°.

Anal. Calcd. for $C_{26}H_{39}N_3O_6$: C, 63.78; H, 8.03; N, 8.58. Found: C, 63.71; H, 8.08; N, 8.32.

EXAMPLE 8

5-(n-HEPTOXY)-4-METHYLPRIMAQUINE

A. 5-(n-Heptoxy)-6-methoxy-4-methyl-8-nitroquinoline

A stirred mixture of 5-hydroxy-6-methoxy-4-methyl-8-nitroquinoline [from Example 7B]—14.0 g, 0.06 mole - n-heptyl bromide (7.5 g, 0.045 mole) and hexamethylphosphoric triamide (12 ml) was heated at 120°, under $N_2$, while a mixture of triethylamine (1 ml) and propylene oxide (6 ml) was added in small portions during 6 hr. Additional propylene oxide (4 ml) was added during 4 hr and the mixture was cooled and filtered and the dull red solid was washed with acetone to return 7.5 g of starting material. The combined filtrate and washings were diluted with water and the resulting solid was extracted with diethyl ether. The extract was washed with 5% sodium hydroxide and water, treated with carbon, dried (sodium sulfate) and evaporated to dryness. Trituration of the dark brown residual oil with petroleum ether (20°–40°) produced a tan solid which was extracted with additional petroleum ether (700 ml). Concentration of the extract to 300 ml and cooling in a Dry-Ice bath gave 7 g (52%) of 5-heptoxy-6-methoxy-4-methyl-8-nitroquinoline as a pale yellow solid, mp 52°–55°. Recrystallization from petroleum ether (20°–40°) provided the analytical sample as glistening pale yellow crystals, mp 56°–57°.

Anal. Calcd. for $C_{18}H_{24}N_2O_4$: C, 65.04; H, 7.28; N, 8.43. Found: C, 64.88; H, 7.32; N, 8.37.

B.
8-Amino-5-(n-heptoxy)-6-methoxy-4-methylquinoline

A stirred mixture of the above nitro compound (3.5 g, 0.01 mole), degreased 40 mesh iron filings (10 g), water (40 ml), acetic acid (5 ml) and dibutyl ether (6 ml) was heated at 100° C. for 3 hr, cooled and filtered. The dark, damp solid was thoroughly extracted with diethyl ether (400 ml) and the extract was concentrated to dryness. The resulting dull green solid was slurried with 50 ml of petroleum ether (bp 20°–40°) and the slurry was cooled to −78° (Dry-Ice acetone), to give 3.5 g of crude product. Crystallization from ligroine (bp 60°–90°) (carbon) gave 2.8 g (88%) of 8-amino-5-heptoxy-6-methoxy-4-methylquinoline as yellow-green crystals, mp 68°–70°. A second crystallization from the same solvent provided the analytical sample, mp 68°–69°.

Anal. Calcd. for $C_{18}H_{26}N_2O_2$: C, 71.49; H, 8.67; N, 9.27. Found: C, 71.33; H, 8.61; N, 9.08.

C.
5-(n-Heptoxy)-6-methoxy-4-methyl-8-(1-methyl-4-phthalimidobutylamino)quinoline A stirred mixture of 3.5 g (0.011 mole) of the foregoing aminoquinoline and 6 g (0.02 mole) of 4-bromo-1-phthalimidopentane was maintained at 140°–145° while triethylamine (3 g) was added in portions during 0.5 hr. Four more increments of 4-bromo-1-phthalimidopentane (3 g) and triethylamine (1 g) were added at 2 hr intervals in the usual manner. The mixture was allowed to cool, diluted with diethyl ether (300 ml) and filtered. The filtrate was treated with carbon and concentrated to dryness. The residue was redissolved in ether and treated with ethereal hydrochloric acid to give a red-orange oil. The oil was separated, triturated with petroleum ether (bp 20°–40°) and basified with excess triethylamine in chloroform. Evaporation to dryness, solution in chloroform, passage through a silica gel column and concentration of the eluate gave 5 g (88%) of the phthalimide derivative as a tan oil. This material was used without further purification.

D.
8-(4-Amino-1-methylbutylamino)-5-heptoxy-6-methoxy-4-methylquinoline Fumarate A stirred mixture of 4 g (0.0078 mole) of the above phthalimido compound, 8 ml of 95% hydrazine and 300 ml of ethanol was heated under reflux for 0.5 hr. In the absence of visible phthalhydrazide formation, 30 ml of chloroform was added to the refluxing solution. Solid formation was evident within 5 min. After 3 hr at reflux, the starting material was completely consumed (tlc). The mixture was allowed to cool, filtered and concentrated in vacuo. The residue was extracted with diethyl ether and the extract was successively washed with potassium hydroxide and water and dried (sodium sulfate). Treatment of the ethereal solution with fumaric acid in acetone followed by crystallization of the resulting yellow solid from acetone (carbon) gave 1.0 g of the fumarate of 5-heptoxy-4-methylprimaquine, mp 145°–148°.

Anal. Calcd. for $C_{27}H_{41}N_3O_6$: C, 64.39; H, 8.21; N, 8.34. Found: C, 64.56; H, 7.92; N, 8.13.

EXAMPLE 9
5-(n-OCTOXY)PRIMAQUINE

A. 6-Methoxy-8-nitro-5-(n-octoxy)quinoline

A stirred mixture of 5-hydroxy-6-methoxy-8-nitroquinoline, (6.6 g, 0.03 mole), n-octylbromide (6.7 g, 0.035 mole) and hexamethylphosphoric triamide (10 ml) was maintained at 125°–130°, under $N_2$, while a mixture of triethylamine (1 ml) and propylene oxide (6 ml) was added in small portions during 3 hr. The mixture was cooled and extracted with petroleum ether (bp 20°–40°) (3 × 100 ml). The extracts were discarded. The petroleum ether-insoluble, semi-solid residue was dissolved in 300 ml of diethyl ether and washed with water, dilute sodium hydroxide and water. The ethereal solution was dried and concentrated in vacuo to leave 8 g of pale brown solid. Crystallization from boiling petroleum ether (20°–40°) (carbon) gave 7.5 g (75%) of the 5-octoxyquinoline derivative, mp 52°–54°. An additional crystallization from petroleum ether did not change the melting point.

Anal. Calcd. for $C_{18}H_{24}N_2O_4$: C, 65.04; H, 7.28; N, 8.43. Found: C, 64.82; H, 7.16; N, 8.28.

B. 8-Amino-6-methoxy-5-(n-octoxy)quinoline

A stirred mixture of the foregoing nitro compound (5 g, 0.015 mole) degreased 40 mesh iron filings (10 g), water (40 ml), acetic acid (6 ml) and butyl ether (6 ml) was heated at 100° for 1.5 hr, cooled and filtered. The dried solid was thoroughly extracted with diethyl ether (total, ca. 400 ml) and acetone (ca. 100 ml) and the combined extracts were evaporated to dryness. Extraction of the residue with petroleum ether (20°–40°) and cooling of the extract in Dry-Ice acetone gave 4 g (89%) of dull green solid, mp 63°–64°. Crystallization from petroleum ether (20°–40°) (Darco) gave 3.5 g of 8-amino-6-methoxy-5-(n-octoxy)quinoline as yellow-green crystals, mp 63°–64°.

Anal. Calcd. for $C_{18}H_{26}N_2O_2$: C, 71.48; H, 8.67; N, 9.26. Found: C, 71.35; H, 8.67; N, 9.18.

C.
6-Methoxy-8-(1-methyl-4-phthalimidobutylamino)-5-(n-octoxy)quinoline A stirred mixture of amino compound from B (13.5 g, 0.044 mole) and 13.5 g of 4-bromo-1-phthalimidopentane was maintained at 140°–145° while 3.5 g of triethylamine was added, dropwise, during 1.5 hr. Two more increments of 4-bromo-1-phthalimidopentane (13.5 g) and triethylamine (3.5 g) were added at 1.5 hr intervals in the usual manner. After a final addition of 4-bromo-1-phthalimidopentane (7 g) and triethylamine (1.5 g) the mixture was allowed to cool and extracted with diethyl ether. The filtered extract was treated with charcoal and diethyl ether-hydrochloric acid to give a viscous red oil. The oil was dissolved in chloroform, washed with dilute sodium hydroxide and water, dried (sodium sulfate), passed through a silica column and stripped of solvent to give 17 g of phthalimido intermediate as a red-orange oil which was used without further purification.

D.

8-(4-Amino-1-methylbutylamino)-6-methoxy-5-(n-octoxy)quinoline Fumarate

A stirred mixture of intermediate from C (17 g, 0.033 mole), ethanol (1500 ml), chloroform (380 ml) and 95% hydrazine (50 ml) was heated under reflux for 2.5 hr. It was concentrated to about half its original volume under reduced pressure, cooled and filtered to remove phthalhydrazide. The filtrate was then concentrated to dryness, in vacuo, leaving 11.1 g of oil. The oil was dissolved in diethyl ether, washed with 30% potassium hydroxide (3×150 ml) and water (until neutral to litmus) and dried (sodium sulfate). Addition of 280 ml of 1% fumaric acid in acetone precipitated the fumarate. Two crystallizations from acetone gave 5.5 g of the 5-octoxyprimaquine fumarate as a yellow solid, mp 152°–154°.

Anal. Calcd. for $C_{27}H_{41}N_3O_6$: C, 64.39; H, 8.21; N, 8.34. Found: C, 64.29; H, 8.23; N, 8.16.

EXAMPLE 10

5-(n-DECOXY)PRIMAQUINE

A. 5-Decoxy-6-methoxy-8-nitroquinoline

A stirred mixture of 6.6 g (0.03 mole) of 5-hydroxy-6-methoxy-8-nitroquinoline, 9.38 g (0.035 mole) of n-decyl iodide and 10 ml of hexamethylphosphoric triamide was maintained at 125°–130°, under $N_2$, while a mixture of triethylamine (1 ml) and propylene oxide (6 ml) was added in small portions during 2 hr. The mixture, which had turned from an initial red to brown, was allowed to cool and extracted with petroleum ether (bp 20°–40°) (3×100 ml). The semi-solid residue was dissolved in 300 ml of diethyl ether and washed with water, dilute sodium hydroxide and water. The dried (sodium sulfate) ethereal solution was concentrated to give a tan solid. Recrystallization from ligroine (bp 60°–90°) (carbon) gave 6 g of 5-decoxy compound, mp 54°–56°. An additional crystallization from ligroine gave the analytical sample as pale yellow crystals, mp 56°.

Anal. Calcd. for $C_{20}H_{28}N_2O_4$: C, 66.63; H, 7.83; N, 7.77. Found: C, 66.47; H, 7.70; N, 7.91.

B. 8-Amino-5-(n-decoxy)-6-methoxyquinoline

A stirred mixture of 4.7 g (0.013 mole) of 5-decoxy-6-methoxy-8-nitroquinoline, 12 g of degreased 40 mesh iron filings, 6 ml of butyl ether, 6 ml of acetic acid and 30 ml of water was heated at 100° for 2 hr, cooled and filtered. The solid was washed with water, dried and extracted with diethyl ether. Evaporation of the diethyl ether, solution of the residue in petroleum ether (20°–40°) and cooling in Dry-Ice acetone gave 3.6 g of pale green solid. Two crystallizations from petroleum ether (20°–40°) (carbon) provided 2.3 g (54%) of amino compound as yellow-green solid, mp 65°.

Anal. Calcd. for $C_{20}H_{30}N_2O_2$: C, 72.70; H, 9.15; N, 8.48. Found: C, 72.66; H, 9.10; N, 8.25.

C.

5-(n-Decoxy)-6-methoxy-8-(1-methyl-4-phthalimidobutylamino)quinoline

A stirred mixture of 3.65 g of 8-amino-5-decoxy-6-methoxyquinoline and 3.5 g of 4-bromo-1-phthalimidopentane was maintained at 140°–145° while 1 g of triethylamine was added in portions during 1.5 hr. Five more increments of 4-bromo-1-phthalimidopentane (3 g) and triethylamine (1 g) were added at 1.5 hr intervals in the usual manner. The mixture was allowed to cool and extracted with diethyl ether (ca. 300 ml). Treatment of the extract with diethyl ether-hydrochloric acid gave a red oil. The oil was dissolved in chloroform (200 ml) washed with dilute sodium hydroxide (2×30 ml) and water, dried (potassium carbonate) passed through a silica column and concentrated to give 3 g of phthalimide derivative as a red oil. This material was used without further purification.

D.

8-(4-Amino-1-methylbutylamino)-5-(n-decoxy)-6-methoxyquinoline Fumarate

A stirred mixture of foregoing phthalimido compound (3 g, 0.0055 mole), 95% hydrazine (14 ml), ethanol (200 ml) and chloroform (100 ml) was heated under reflux for 2 hr, allowed to cool and filtered. The solvent was removed in vacuo and the residue was extracted with diethyl ether. The extract was washed with 30% potassium hydroxide (3×30 ml), water (until neutral) and dried (sodium sulfate). Treatment with an excess of 1% fumaric acid in acetone gave a yellow solid. Crystallization from acetone twice (charcoal) provided 1.5 g of 5-decoxyprimaquine fumarate, mp 156°–161°.

Anal. Calcd. for $C_{29}H_{45}N_3O_6$: C, 65.51; H, 8.53; N, 7.90. Found: C, 65.43; H, 8.79; N, 8.01.

EXAMPLE 11

5-(n-DODECOXY)-4-METHYLPRIMAQUINE

A. 5-Dodecoxy-6-methoxy-4-methyl-8-nitroquinoline

A stirred mixture of 5-hydroxy-6-methoxy-4-methyl-8-nitroquinoline (11.7 g, 0.05 mole; prepared as given in Example 7B), n-dodecyl bromide (16 g, 0.065 mole), triethylamine (0.5 ml) and hexamethylphosphoric triamide (15 ml) was heated at 140°–145° while 15 ml of propylene oxide was added in small portions during 1 hr. An additional 2 g of n-dodecyl bromide was added, dropwise, during 0.5 hr and heating was then continued for a half hour more. The mixture was cooled and extracted with 200 ml of diethyl ether leaving 5.8 g of unreacted starting material. The extract was washed with dilute sodium hydroxide and water and dried (sodium sulfate). Evaporation of the solvent left a dark oil which on solution in 100 ml of petroleum ether (20°–40°) and cooling in Dry-Ice acetone gave 8.5 g of the 5-dodecoxy compound. An additional crystallization from petroleum ether (20°–40°) afforded the analytical sample, mp 55°–57°.

Anal. Calcd. for $C_{23}H_{34}N_2O_4$: C, 68.63; H, 8.51; N, 6.96. Found: C, 68.64; H, 8.55; N, 6.84.

B. 8-Amino-5-dodecoxy-6-methoxy-4-methylquinoline

A stirred mixture of the foregoing nitro compound (9 g, 0.022 mole), degreased 40 mesh iron filings (18 g), water (60 ml), acetic acid (8 ml) and dibutyl ether (10 ml) was heated at 85°–90° for 1.25 hr and at 100° for 0.25 hr. The mixture was cooled and filtered and the solid was washed with water, dried and thoroughly extracted with diethyl ether (total, 600 ml). The extract was treated with carbon and concentrated to give 7.7 g of pale green solid. Solution of this material in petroleum ether (20°–40°) and cooling in Dry-Ice acetone provided 7 g (84%) of 8-amino-5-dodecoxy-6-methoxy-4-methylquinoline, mp 53°–55°. The analytical sample was obtained by recrystallization from petroleum ether (20°–40°), mp 55°–56°.

Anal. Calcd. for $C_{23}H_{36}N_2O_2$: C, 74.16; H, 9.74; N, 7.52. Found: C, 74.13; H, 9.49; N, 7.65.

C.
5-Dodecoxy-6-methoxy-4-methyl-8-(1-methyl-4-phthalimidobutylamino)quinoline A stirred mixture of 5 g (0.013 mole) of the above aminoquinoline and 5 g (0.016 mole) of 4-bromo-1-phthalimidopentane was maintained at 140°–145° while triethylamine (2.5 ml) was added in small portions during 30 min. Two more increments of 4-bromo-1-phthalimidopentane (5 g) and triethylamine (2.5 ml) were added at 1.5 hr intervals in the usual manner. The mixture was allowed to cool, diluted with acetone (200 ml) and filtered to remove triethylamine hydrobromide. The filtrate was treated with carbon and the solvent was evaporated in vacuo. Extraction of the residue with diethyl ether and treatment of the filtered extract with diethyl ether-hydrochloric acid gave a red-brown oil. This material was dissolved in chloroform, basified with dilute sodium hydroxide, washed with water and dried (sodium sulfate). Evaporation of the solvent, in vacuo, gave 7 g (91%) of the title phthalimide derivative as a brown oil which was used without further purification.

D.
8-(4-Amino-1-methylbutylamino)-5-dodecoxy-6-methoxy-4-methylquinoline Fumarate A stirred mixture of the intermediate phthalimide type above (9 g, 0.015 mole), 95% hydrazine (40 ml), ethanol (240 ml) and chloroform (120 ml) was heated under reflux for 2 hr, cooled and filtered. The filtrate was evaporated under reduced pressure and the residue was extracted with diethyl ether. The filtered extract was washed with 30% potassium hydroxide (3×50 ml) and water and dried (sodium sulfate). The ether solution was treated with 1% isopropanolic fumaric acid to give 4.2 g of a tacky yellow solid. Two crystallizations from acetone gave 2.1 g of 5-(n-dodecoxy)-4-methylprimaquine fumarate as a yellow solid, mp 147°–155°.

Anal. Calcd. for $C_{32}H_{51}N_3O_6$: C, 66.99; H, 8.96; N, 7.32. Found: C, 66.69; H, 8.76; N, 7.30.

TABLE 1

COMPARISON OF THE ANTIMALARIAL ACTIVITY OF PRIMAQUINE AND 4-METHYLPRIMAQUINE

| | Suppressive Activity P. berghei, Rane Mouse Test Dose, mg/kg; ΔMST, Days; 5 mice | | | | | Radical Curative Activity P. cynomolgi, Seato Rhesus Dose, mg/kg (×7) | | | |
|---|---|---|---|---|---|---|---|---|---|
| Compound | 40 | 80 | 160 | 320 | 640 | 3.16 | 1.3 | 1.0 | 0.316 |
| Primaquine Diphosphate | I | I | 9(A) | 2/5T | 5T | 6/6C | 1/2C | | 0/2C |
| 4-Methylprimaquine Diphosphate | I | I | 9(A) | 10(A) | 3C,1T | | 2/2C | | 0/4C |

Legend:
I = Inactive, A = Active, increase in survival time at 7 days or more relative to controls;
T = Toxic Death, C = Cures.

TABLE 2

ANTIMALARIAL EFFECTS OF 5-(OR) PRIMAQUINE TYPES

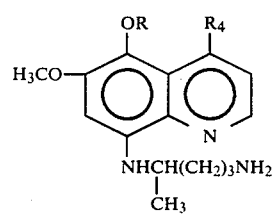

| | | | Blood Schizonticidal Effects Suppressive Activity on P. berghei (mice) Dose, mg/kg/Increase in survival, days @ 5 mice | | | | | | Tissue Schizonticidal Effects Radical Curative Activity: P. cynomolgi (rhesus) Dose, mg/kg | | | | |
|---|---|---|---|---|---|---|---|---|---|---|---|---|---|
| Example No. | 5-OR | R4 | 20 | 40 | 80 | 160 | 320 | 640 | 0.25 | 0.316 | 1.0 | 1.3 | 3.16 | 10 |
| 1 | $OCH_2CH_3$ | H | | 0.3 | | 3T | | 5T | | | | | | |
| 2 | $OCH_2CF_3$ | H | | | | | | | | 0/1C | 1/1C | | | |
| 3 | $OCH_2CH_2CH_3$ | H | 4.5 | 8.3 | 1T/9.4 | 5T | 5T | 5T | | 2/2C | 3/3C | | | 1/1C |
| 4 | $O(CH_2)_3CH_3$ | H | 6.5 | 6.9 | 2T/5.6 | 3T | | 5T | | 2/4C | 2/2C | | | T |
| 6 | $O(CH_2)_5CH_3$ | H | 3.7 | 6.5 | 1C | 1C | 0.1 | 1T | | 0/2C | 3/3C | | | 1/1C |
| 7 | $O(CH_2)_5CH_3$ | $CH_3$ | 5C | 5C | 4C/1T | 5T | 5T | 5T | | 1/1C | 1/1C | | 0/1C | |
| 8 | $O(CH_2)_6CH_3$ | $CH_3$ | 5C | 5C | 2C/3T | 5T | 5T | 5T | | | | | | T |
| 11 | $O(CH_2)_{11}CH_3$ | $CH_3$ | 3.2 | 6.4 | 7.6 | 4C | 5C | 5C | | | 0/1C | | | |

Legend:
C = Cures; T = Toxic Death

TABLE 3
ANTIMALARIAL EFFECTS OF SELECTED 5-(OR) PRIMAQUINE TYPES

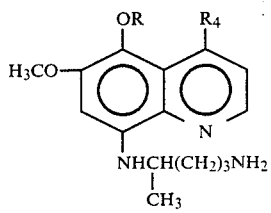

| | | | Blood Schizonticidal Effects Suppressive Activity on *P. berghei* (mice) Dose, mg/kg/Increase in survival, days @ 5 mice | | | | | | | | Tissue Schizonticidal Effects Radical Curative Activity: *P. cynomolgi* (rhesus) Dose, mg/kg | | | | |
|---|---|---|---|---|---|---|---|---|---|---|---|---|---|---|---|
| Example No. | 5-OR | $R_4$ | 2.5 | 5 | 10 | 20 | 40 | 80 | 160 | 320 | 640 | 0.1 | 0.316 | 1.0 | 3.16 | 10 |
| 3 | $O(CH_2)_2CH_3$ | H | | | | 4.5 | 8.3 | 1T/9.4 | 5T | 5T | 5T | 0/2C | 2/2C | 3/3C | | 1/1C |
| 5 | $O(CH_2)_4CH_3$ | $CH_3$ | | | | | | | | | | | | | | |
| 6 | $O(CH_2)_5CH_3$ | H | | | | 3.7 | 6.5 | 1C | 1C | 0.1 | 1T | | 0/2C | 3/3C | | 1/1C |
| 7 | $O(CH_2)_5CH_3$ | $CH_3$ | 1C | 1C | 1C | 5C | 5C | 4C/1T | 5T | 5T | 5T | 4/4C | 1/1C | 1/1C | 0/1C | |
| 11 | $O(CH_2)_{11}CH_3$ | $CH_3$ | | | | 3.2 | 6.4 | 7.6 | 4C | 5C | 5C | 0/1C | | 0/1C | | |

Legend:
C = Cures; T = Toxic Death. Detailed studies done on free base showed no relapses to 30 days following treatment with 0.5 mg/kg and 1.0 mg/kg; in most instances, 0.25 mg/kg achieved cures with some relapses after 12 days or 20 days; 0.125 mg/kg led to relapses after 12 days.

We claim:
1. A compound of the formula,

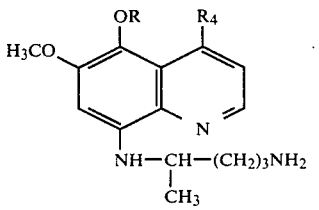

wherein $R_4$ represents hydrogen or methyl; R represents a straight-chain alkyl group having 3 to 12 carbon atoms; and pharmaceutically acceptable acid addition salts thereof wherein the salt forming acid is selected from the group consisting of hydrochloric acid, phosphoric acid, nitric acid, sulfamic acid, sulfuric acid, maleic acid, fumaric acid, citric acid, beta-resorcylic acid and pamoic acid.

2. The compound of claim 1 wherein $R_4$ is methyl.
3. The compound of claim 1 wherein $R_4$ is hydrogen.
4. The compound of claim 2 wherein R represents a straight-chain alkyl group having 4 to 8 carbon atoms.
5. The compound of claim 3 wherein R represents a straight-chain alkyl group having 4 to 8 carbon atoms.
6. The compound of claim 2 wherein R is n-hexyl.
7. The compound of claim 2 wherein R is n-heptyl.
8. The compound of claim 2 wherein R is n-dodecyl.
9. The compound of claim 3 wherein R is n-propyl.
10. The compound of claim 3 wherein R is n-butyl.
11. The compound of claim 3 wherein R is n-hexyl.
12. A method for treating malaria caused by the presence of malaria parasites in the blood, formed tissues, or blood and formed tissues which comprises the step of administering parenterally or orally to an infected animal an antimalarial effective amount of a compound having the formula:

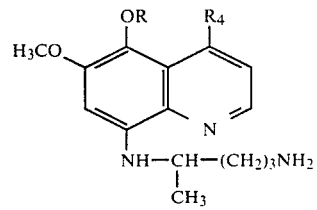

wherein $R_4$ represents hydrogen or methyl; R represents a straight-chain alkyl group having 3 to 12 carbon atoms; and pharmaceutically acceptable acid addition salts thereof wherein the salt forming acid is selected from the group consisting of hydrochloric acid, phosphoric acid, nitric acid, sulfamic acid, sulfuric acid, maleic acid, fumaric acid, citric acid, beta-resorcyclic acid and pamoic acid.

13. The method of claim 12 wherein $R_4$ is methyl.
14. The method of claim 12 wherein R represents a straight-chain alkyl group having 4 or more carbon atoms.
15. The method of claim 14 wherein R represents a straight-chain alkyl group having 4 to 8 carbon atoms.
16. The method of claim 14 wherein R represents a straight-chain alkyl group having 4 to 12 carbon atoms.
17. The method of claim 16 wherein R is n-hexyl.
18. The method of claim 16 wherein R is n-heptyl.
19. The method of claim 16 wherein R is n-dodecyl.
20. The method of claim 12 wherein $R_4$ is hydrogen.
21. The method of claim 20 wherein R represents a straight-chain alkyl group containing 4 or more carbon atoms.
22. The method of claim 20 wherein R represents a straight-chain alkyl group containing 4 to 8 carbon atoms.
23. The method of claim 20 wherein R is n-propyl.
24. The method of claim 20 wherein R is n-butyl.
25. The method of claim 20 wherein R is n-hexyl.
26. A method for treating malaria caused by the presence of malaria parasites in the blood, formed tissues, or blood and formed tissues which comprises the step of administering orally to an infected animal an antimalarial effective amount of a compound having the formula:

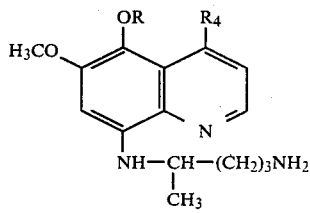

wherein $R_4$ represents hydrogen or methyl; R represents a straight-chain alkyl group having 3 to 12 carbon atoms; and pharmaceutically acceptable salts thereof wherein the salt forming acid is selected from the group consisting of hydrochloric acid, phosphoric acid, nitric acid, sulfamic acid, sulfuric acid, maleic acid, fumaric acid, citric acid, beta-resorcylic acid and pamoic acid which has been admixed with an excipient selected from the group consisting of lactose, precipitated chalk, dibasic calcium phosphate, microcrystalline cellulose derivatives, maize starch, talc and calcium stearate.

27. A method for treating malaria caused by the presence of malaria parasites in the blood, formed tissues, or blood and formed tissues which comprises the step of administering parenterally to an infected animal an antimalarial effective amount of a compound having the formula:

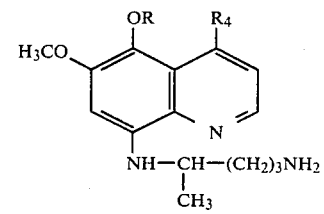

wherein $R_4$ represents hydrogen or methyl; R represents an alkyl group having 3 to 12 carbon atoms; and pharmaceutically acceptable salts thereof wherein the salt forming acid is selected from the group consisting of hydrochloric acid, phosphoric acid, nitric acid, fumaric acid, citric acid, beta-resorcylic acid, and pamoic acid which has been admixed with an aqueous solution of an ethoxylated sorbitan fatty acid ester.

28. The method of claim 27 wherein the aqueous solution contains a thickener selected from the group consisting of carboxymethyl cellulose and polyethylene glycol.

* * * * *